United States Patent [19]
Banik et al.

[11] Patent Number: 5,779,648
[45] Date of Patent: *Jul. 14, 1998

[54] MULTI-MOTION CUTTER MULTIPLE BIOPSY SAMPLING DEVICE

[75] Inventors: Michael S. Banik, Cincinnati, Ohio; Donald E. Robinson, Hopkinton, Mass.

[73] Assignee: Boston Scientific Corporation, Natick, Mass.

[*] Notice: The term of this patent shall not extend beyond the expiration date of Pat. No. 5,471,992.

[21] Appl. No.: 820,411

[22] Filed: Mar. 12, 1997

Related U.S. Application Data

[63] Continuation of Ser. No. 557,916, Nov. 14, 1995, abandoned, which is a continuation of Ser. No. 380,202, Jan. 30, 1995, Pat. No. 5,471,992, which is a continuation of Ser. No. 193,298, Feb. 8, 1994, abandoned.

[51] Int. Cl.$^6$ .................................................. A61B 5/00
[52] U.S. Cl. .................................................. 600/567
[58] Field of Search .......................... 128/749, 751–754; 606/167, 170

[56] References Cited

U.S. PATENT DOCUMENTS

| | | |
|---|---|---|
| 612,569 | 10/1898 | Moscrop. |
| 668,647 | 2/1901 | Jaenicke. |
| 1,162,901 | 12/1915 | Cantey. |
| 1,606,497 | 11/1926 | Berger. |
| 1,867,624 | 7/1932 | Hoffman. |
| 1,891,054 | 12/1932 | Pitman. |
| 2,426,535 | 8/1947 | Turkel. |
| 2,493,979 | 1/1956 | Kudd. |
| 2,541,542 | 2/1951 | Perez et al.. |
| 2,749,909 | 6/1956 | Ullery et al. ......................... 128/2 |
| 3,001,522 | 9/1961 | Silverman. |
| 3,147,749 | 9/1964 | Marsh ......................... 128/2 |
| 3,175,554 | 3/1965 | Stewart. |
| 3,181,533 | 5/1965 | Heath. |
| 3,342,175 | 9/1967 | Bulloch. |
| 3,477,423 | 11/1969 | Griffith ......................... 128/2 |
| 3,683,892 | 8/1972 | Harris ......................... 128/2 |
| 3,692,020 | 9/1972 | Schied ......................... 128/2 |
| 3,732,858 | 5/1973 | Banko ......................... 128/2 |
| 3,882,849 | 5/1975 | Jamshidi ......................... 128/2 |
| 3,902,498 | 9/1975 | Niederer. |
| 3,903,892 | 9/1975 | Komiya ......................... 128/303 |
| 3,924,608 | 12/1975 | Mitsui ......................... 128/2 B |
| 3,955,578 | 5/1976 | Chamness et al. ......................... 128/303 |
| 3,989,033 | 11/1976 | Halpern et al. ......................... 128/2 |
| 3,989,049 | 11/1976 | Yoon ......................... 128/326 |
| 3,996,935 | 12/1976 | Banko ......................... 128/276 |
| 4,007,732 | 2/1977 | Kvavle et al.. |

(List continued on next page.)

FOREIGN PATENT DOCUMENTS

| 1215439 | 12/1970 | United Kingdom. |
|---|---|---|
| WO 93/046304 | 3/1993 | WIPO. |

OTHER PUBLICATIONS

Radial Jaw Single-Use Biopsy Forseps, Boston Scientific Corporation, 1993.

Grossman, "Gastrointestinal Endoscopy", Clinical Symposia, vol. 32, No. 3, 1980.

Primary Examiner—Max Hindenberg
Attorney, Agent, or Firm—Finnegan, Henderson, Farabow, Garrett & Dunner, L.L.P.

[57] ABSTRACT

An instrument for obtaining tissue samples from a site deep within the body. The instrument has an elongated proximal portion that is constructed to follow a long, torturous path to the site and a distal end constructed to remove a tissue sample from the body, including tissue specimens, polyps or the like. The instrument is constructed to take multiple biopsy samples without being withdrawn from the body by including a device body defining a storage space along the axis of the device suitable for storage of multiple, successively taken samples. The instrument includes a sampling assembly having a cutting member, constructed such that it can be actuated in a first, rotary motion to take a tissue sample from the body and a second, axial motion for disposing the sample axially into the storage space.

25 Claims, 8 Drawing Sheets

U.S. PATENT DOCUMENTS

| | | | |
|---|---|---|---|
| 4,020,847 | 5/1977 | Clark | 128/751 |
| 4,168,698 | 9/1979 | Ostergard | 128/751 |
| 4,174,715 | 11/1979 | Hasson | 128/321 |
| 4,178,810 | 12/1979 | Takahashi | 74/501 |
| 4,200,111 | 4/1980 | Harris | 128/751 |
| 4,220,155 | 9/1980 | Kimberling et al. . | |
| 4,243,048 | 1/1981 | Griffin . | |
| 4,282,884 | 8/1981 | Boebel | 128/751 |
| 4,326,530 | 4/1982 | Fleury, Jr. | 128/303 |
| 4,427,014 | 1/1984 | Bel et al. | 128/751 |
| 4,461,305 | 7/1984 | Cibley | 128/754 |
| 4,493,320 | 1/1985 | Treat | 128/303 |
| 4,522,206 | 6/1985 | Whipple et al. | 128/312 |
| 4,574,803 | 3/1986 | Storz | 128/305 |
| 4,620,547 | 11/1986 | Boebel | 128/754 |
| 4,651,752 | 3/1987 | Fuerst . | |
| 4,651,753 | 3/1987 | Lifton | 128/751 |
| 4,662,371 | 5/1987 | Whipple et al. | 128/312 |
| 4,682,606 | 7/1987 | DeCaprio . | |
| 4,693,257 | 9/1987 | Markham | 128/752 |
| 4,708,147 | 11/1987 | Haaga . | |
| 4,712,550 | 12/1987 | Sinnett . | |
| 4,735,215 | 4/1988 | Goto et al. | 128/754 |
| 4,763,668 | 8/1988 | Macek et al. | 128/751 |
| 4,785,826 | 11/1988 | Ward . | |
| 4,817,630 | 4/1989 | Schintgen et al. | 128/751 |
| 4,830,002 | 5/1989 | Semm | 128/321 |
| 4,867,156 | 9/1989 | Stack et al. | 128/305 |
| 4,881,550 | 11/1989 | Kothe | 128/752 |
| 4,887,612 | 12/1989 | Esser et al. | 128/751 |
| 4,903,709 | 2/1990 | Skimmer | 128/754 |
| 4,926,877 | 5/1990 | Bookwalter | 128/754 |
| 4,936,845 | 6/1990 | Stevens . | |
| 4,953,559 | 9/1990 | Salerno | 128/751 |
| 4,971,067 | 11/1990 | Bolduc et al. | 128/751 |
| 4,976,269 | 12/1990 | Mehl | 128/754 |
| 4,986,825 | 1/1991 | Bays et al. | 604/22 |
| 5,026,379 | 6/1991 | Yoon | 606/141 |
| 5,052,402 | 10/1991 | Bencini et al. | 128/751 |
| 5,074,311 | 12/1991 | Hasson | 128/754 |
| 5,085,659 | 2/1992 | Rydell . | |
| 5,098,440 | 3/1992 | Hillstead | 606/108 |
| 5,111,828 | 5/1992 | Kornberg et al. | 128/754 |
| 5,133,360 | 7/1992 | Spears . | |
| 5,133,727 | 7/1992 | Bales et al. | 606/170 |
| 5,147,378 | 9/1992 | Markham | 606/206 |
| 5,148,813 | 9/1992 | Bucalo | 128/754 |
| 5,171,255 | 12/1992 | Rydell . | |
| 5,172,700 | 12/1992 | Bencini et al. | 128/751 |
| 5,195,533 | 3/1993 | Chin et al. | 128/754 |
| 5,197,484 | 3/1993 | Kornberg et al. | 128/754 |
| 5,211,655 | 5/1993 | Hasson | 606/205 |
| 5,224,488 | 7/1993 | Neuffer | 128/751 |
| 5,238,002 | 8/1993 | Devlin et al. | 128/751 |
| 5,242,461 | 9/1993 | Kortenbach et al. . | |
| 5,251,641 | 10/1993 | Xavier | 128/754 |
| 5,267,572 | 12/1993 | Bucalo | 128/754 |
| 5,331,971 | 7/1994 | Bales et al. | 128/751 |
| 5,342,390 | 8/1994 | Slater et al. | 606/205 |
| 5,373,854 | 12/1994 | Kolozsi . | |
| 5,375,608 | 12/1994 | Tiefenbrun et al. . | |
| 5,383,471 | 1/1995 | Funnell | 128/751 |
| 5,394,887 | 3/1995 | Haaga | 128/740 |

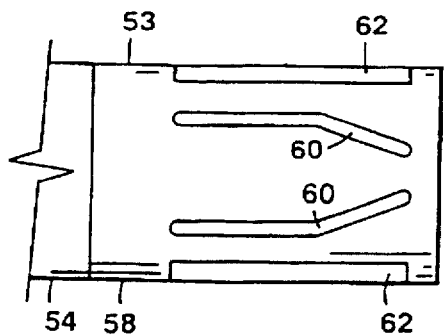
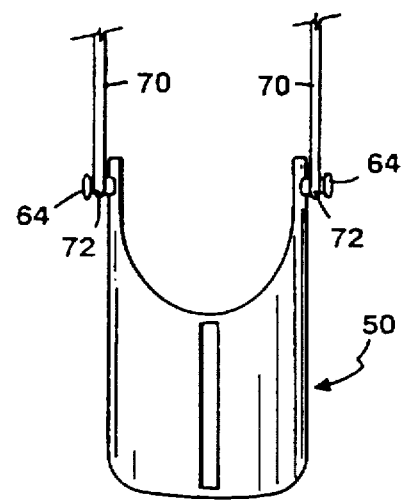
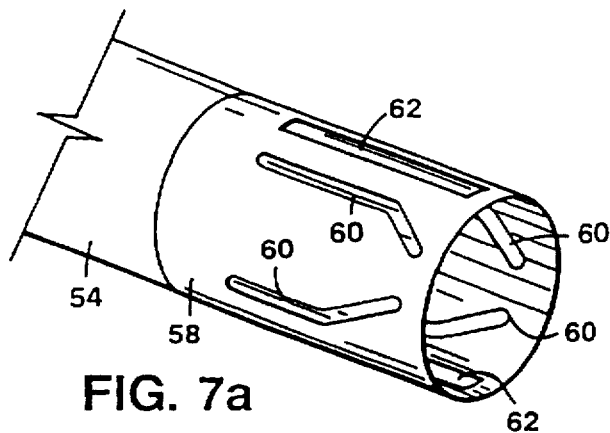
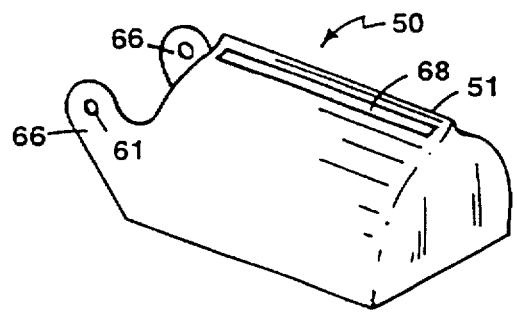
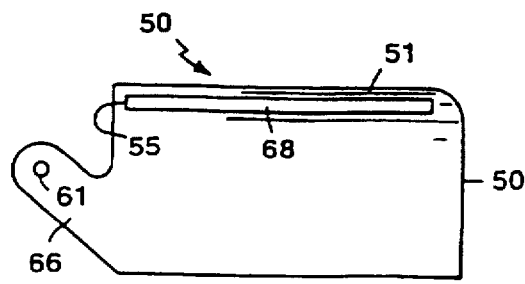
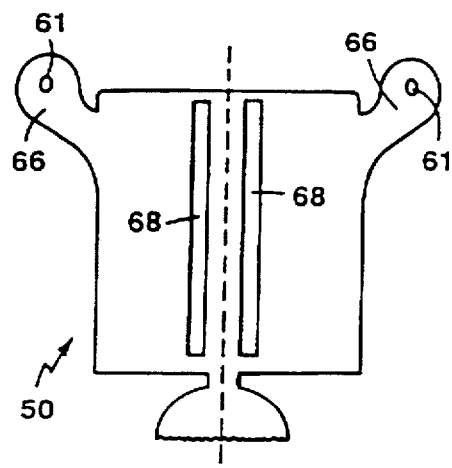
FIG. 7
FIG. 7c
FIG. 7a
FIG. 7d
FIG. 7b
FIG. 7e

MULTI-MOTION CUTTER MULTIPLE BIOPSY SAMPLING DEVICE

CROSS REFERENCE TO RELATED APPLICATIONS

This is a continuation of application Ser. No. 08/557,916 filed Nov. 14, 1995, now abandoned; which is a continuation of Ser. No. 08/380,202 filed on Jan. 30, 1995, now U.S. Pat. No. 5,471,992; which is a continuation of Ser. No. 08/193,298 filed on Feb. 8, 1994, now abandoned.

FIELD OF THE INVENTION

This invention relates to taking samples of tissue from the body.

BACKGROUND OF THE INVENTION

Tissue samples can be examined in a laboratory to determine the presence of a pathological disorder (e.g. malignancy). Often, the samples must be obtained from deep within the body using a medical sampling instrument. It is usually best to obtain several samples around the location where the disorder is suspected so that the presence and progress of disease, if any, can be accurately determined. The samples must be catalogued according to the location from which each sample is taken and the integrity of the samples must be maintained for the subsequent laboratory analysis.

SUMMARY OF THE INVENTION

In an aspect, the invention features an instrument for obtaining tissue samples from a site deep within the body. The instrument has an elongated proximal portion that is constructed to follow a long, torturous path to the site and a distal end constructed to remove a tissue sample from the body, including tissue specimens, polyps or the like. The instrument is constructed to take multiple biopsy samples without being withdrawn from the body by including a device body defining a storage space along the axis of the device suitable for storage of multiple, successively taken samples. The instrument includes a sampling assembly having a cutting member, constructed such that it can be actuated in a first, rotary motion to take a tissue sample from the body and a second, axial motion for disposing the sample axially into the storage space.

Embodiments may include one or more of the following features. The cutting member is a jaw-like member, the first motion is a radial jaw opening and closing motion, and the second motion is an axial motion wherein the sample is pulled by the jaw-like member into the storage space. The instrument includes a second jaw-like cutting member that is constructed for radial motion and is axially stationary. The first jaw-like cutting member is constructed such that it can be actuated to move transversely into space defined by the second jaw-like member to engage a sample cut by the members prior to the axial motion. The cutting member is attached to a tubular member defining the storage space. The tubular member and cutting member include a slot and pin camming arrangement constructed to allow the motions by relative axial movement of the tubular member and the cutting member. The slot is provided on the cutting member and the pin is provided on the tubular member. The camming arrangement provides, in order, opening motion of the cutting member, closing motion of the cutting member, transverse motion of the cutting member to facilitate engagement with a sample cut by the member, axial motion for disposing the sample in the storage space, and axial motion for returning the cutting member to a position in preparation for taking another sample. The instrument includes a second jaw like member that is constructed for radial and axial motion. The first and second jaws are coupled to the instrument at a distal end portion that is rigid relative to a flexible portion proximal thereof. The rigid distal end portion has an axial length that is about equal to or shorter than the axial length of the jaws. The rigid distal end portion defines a space that has an axial length that is about equal to the axial length of the jaws and the jaws are moveable proximally within the distal end portion. The distal end portion has a length of about 57 mm.

Other features, advantages and methods of use follow.

BRIEF DESCRIPTION OF THE DRAWING

We first briefly describe the drawings.

FIG. 6 is a side view of another embodiment with the jaws open, while

FIGS. 7, 7a–7e are views of components of the embodiment of FIG. 6, including a side view of a coupling section (FIG. 7), a perspective view of the coupling section (FIG. 7a), a side view of a jaw (FIG. 7b), a top view of a jaw (FIG. 7c), a perspective view of a jaw (FIG. 7d), and a top view showing a stamped cut piece of metal that can be subsequently formed into a jaw (FIG. 7e).

DESCRIPTION OF THE PREFERRED EMBODIMENTS

Figure 1:
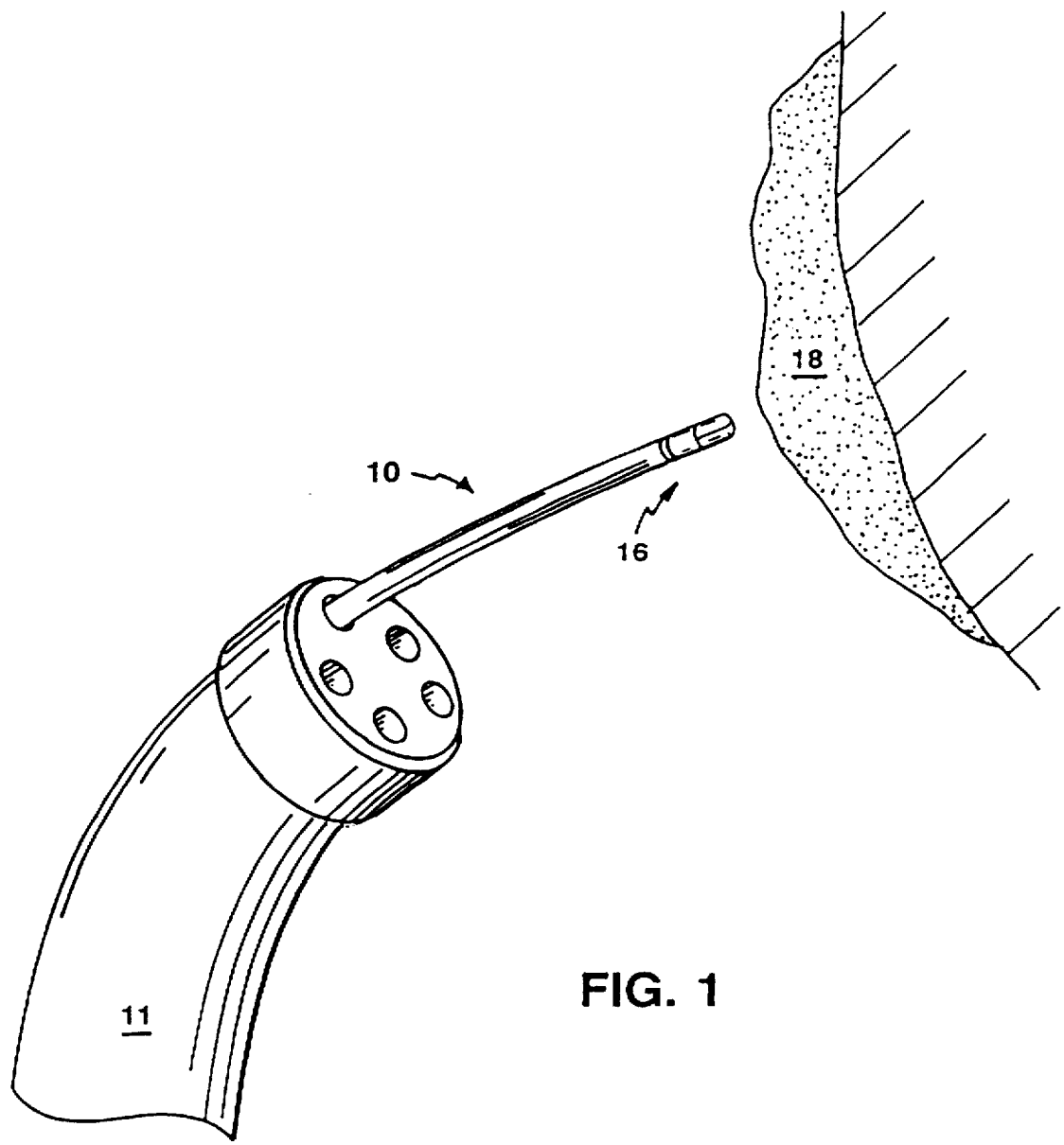
FIG. 1 is a perspective view of an embodiment of the invention being delivered into the body through an endoscope.

Referring to FIG. 1, the device 10 for multiple biopsy sampling may be delivered into the body through the channel of an endoscope device 11 (e.g., gastroscope, sigmoidoscope, or colonoscope). The endoscope device typically has a length of about 100–250 cm and a channel diameter of 2.0–3.8 mm, typically about 2.8 mm. A distal sampling portion 16 is extended from the endoscope for cutting and storing a sample of tissue from a body surface 18 of a patient (e.g. from a surface in the gastrointestinal tract or bronchial tract). The device has a diameter of preferably around 1.8–2.4 mm, typically about 2.3 mm or less and is of sufficient flexibility so it passes easily though the channel when the endoscope follows a tortuous body passageway. The endoscope may include other lumens for water, air, suction, and viewing, for example. Devices according to the invention can be adapted to be introduced to sites (e.g., urinary tract, reproductive organs, cardiac tissue, or the like) deep within the body by other means. For example, a device can be configured with a lumen so that it can be advanced over a guidewire, e.g., in vascular applications. The device may be passed through an introducer or guiding catheter in, e.g., cardiac applications. The sampling and storage arrangements may be useful in open surgery applications.

Figure 2:
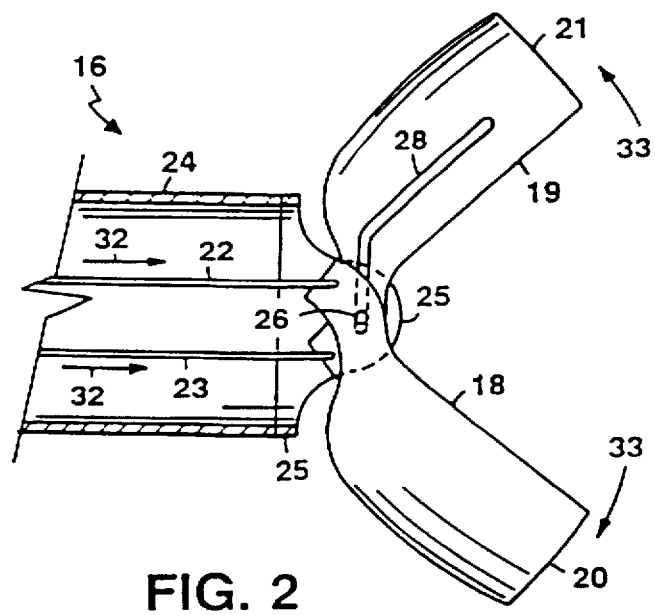
FIG. 2 is a cross-sectional view of an embodiment with the jaws open.
Figure 3:
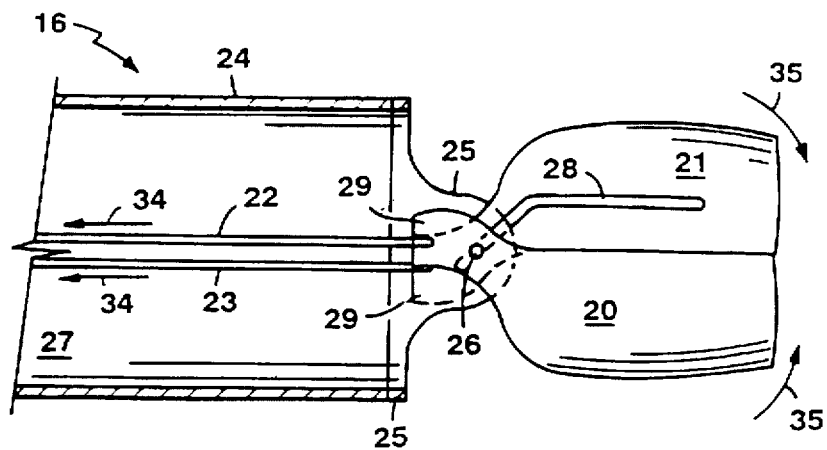
FIG. 3 is a cross-sectional view of an embodiment of the invention with the jaws closed.
Figure 4:
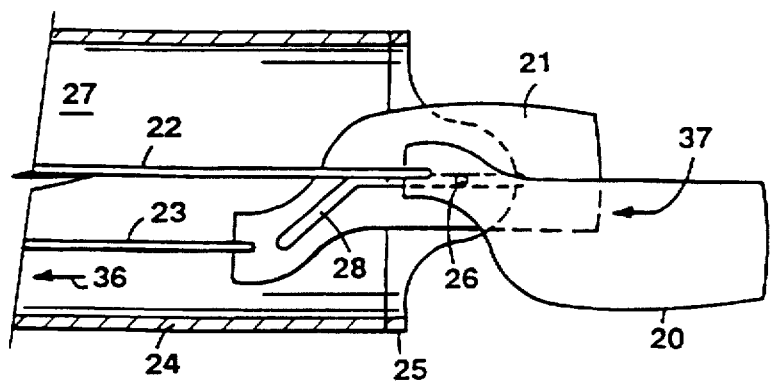
FIG. 4 is a cross-sectional side view with one of the jaws retracted.

Referring particularly to FIGS. 2–4, the sampling portion 16 includes jaws 20, 21, coupling section 25, control wires 22, 23, and sleeve 24. All or part of surfaces 18 and 19, on jaws 20, 21, may be sharpened or serrated to facilitate cutting. Each jaw 20 and 21 also has ear-forms 29. Control wires (or rods) 22, 23 are connected to the proximal end of ear-forms 29 and are used to radially open and close jaws 20 and 21 by manipulating the control wires 22, 23 from outside the body, as will be discussed further below on jaw 20, ear-form 29 has a bore 30 and on jaw 21 ear-form 29 has a cam slot 28. Jaws 20 and 21 are attached to sleeve 24 by rigid coupling section 25 using pivot pins 26. Pivot pins 26 are cantilevered from coupling section 25 and extend through cam slot 28 and bore 30. Sleeve 24 has storage space 27 to store at least, preferably five or more, samples.

Figure 2A:
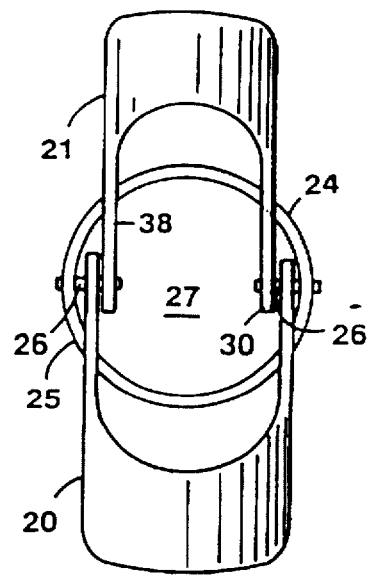
FIG. 2a is an end-on cross-sectional view of the embodiment with the jaws open.
Figure 2B:
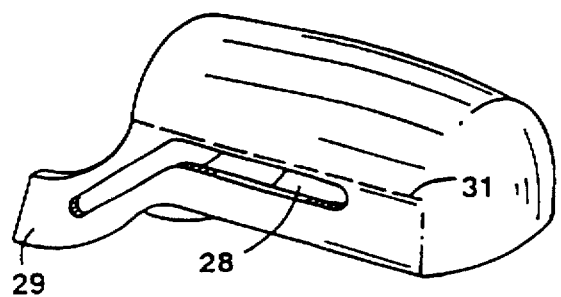
FIG. 2b is a perspective view of one of the jaws.

Ear-forms 29 are constructed so they act in cooperation with pivot pins 26 such that axial force by the control wires 22, 23 is cammed to radial motion of jaws 20, 21. Cam slot 28 in jaw 21 has a width of about 0.003 inch and is formed in the side flattened portion 31 of jaw 21. Side flattened portion 31 is about 0.005–0.006 inch wide (FIG. 2b). The axial length of jaw 21 is about 5–7 mm. Jaw 21 is slightly shorter and narrower than jaw 20 so that jaw 21 can fit at least partially inside jaw 20, as will be discussed below. The circumferential shape of the jaws 20, 21 must be complementary to the shape of the coupling section 25 and storage space 27 so that travel along the cam slot 28 does not cause transverse motion of the jaws 20, 21.

Referring particularly to FIG. 2, with control wires 22, 23 pushed distally, the jaws are forced into an open position by radial rotation about the pivot axis defined by the pins 26 (arrows 32, 33). Referring particularly to FIG. 3, with control wires 22, 23 pulled proximally, the jaws are forced into a closed position (arrows 34, 35). Referring particularly to FIG. 4, with control wire 23 pulled further proximally, the jaw 21, following a path defined by the cam slot 28, first moves transversely into the space defined by jaw 20, to grasp or capture the sample that has been cut (not shown), and then proximally, to draw the sample into storage space 27 (arrows 36, 37). The proximal portion of jaw 21 includes a cutaway 38 (see FIG. 2a) so that jaw 21 does not bind on a sample which has been placed in storage space 27 as jaw 21 moves distally from the storage space to prepare to cut another sample.

The pivot pins 26 are cantilevered from coupling section 25 so as not to extend across the diameter of the device thus providing a relatively large storage space 27 for storing samples. Previous samples can be stored in storage space 27 while succeeding samples are taken, thus allowing multiple samples to be taken without removing the device from the endoscope. Sleeve 24 may include lumens (not shown) for control wires 22, 23 to separate the control wires 22, 23 from samples stored inside the storage space 27 and enable the control wires 22, 23 to move freely.

In alternative embodiments, the sample storage space may include a barbed spear-form member (not shown), e.g., a stationary or axially moveable barbed spear-form, to pierce the samples and hold them in place. The axially moveable jaw 21 may include a member extending from the control portion 29, radially across the space 27. This member bears on previously taken samples to help urge them proximally as a succeeding sample is being drawn proximally into the space by jaw 21. The member can be made flexible or adjustable so that it does not push the last taken sample distally as the jaw 21 moves distally to prepare to take an additional sample. Further, a separate, axially moveable rake-type member could be provided to bear on previously taken samples to help urge them proximally as a succeeding sample is being drawn proximally into the space by jaw 21.

An advantage of this embodiment is that the distal end of the device is rigid for only a relatively short axial length, which makes it easier to thread the device through tortuous passageways with sharp curves. In the preferred embodiment, only the jaws 20, 21 and the short coupling section 25 (total length, typically 5–14 mm) are relatively rigid. These components are formed of metal or a stiff polymer such as Ultem (polyetheramide, General Electric) that can withstand the forces applied during jaw actuation. The proximal portion, such as the sleeve 24, is highly flexible. It is formed of a flexible polymer and/or surrounded by a flexible coil. The storage portion therefore, may also be flexible for most of its length. The device can be configured to take and store many samples, e.g., greater than fifteen, from a highly tortuous body passage way due to the short, stiff distal portion and long, flexible sleeve 24. In embodiments, both of the jaws can be made axially moveable. In this case, the stiff coupling section 25 may be of comparable length to jaws 20, 21 so the jaws 20, 21 can be placed inside the coupling section 25 during entry into and removal from the body.

Figure 5:
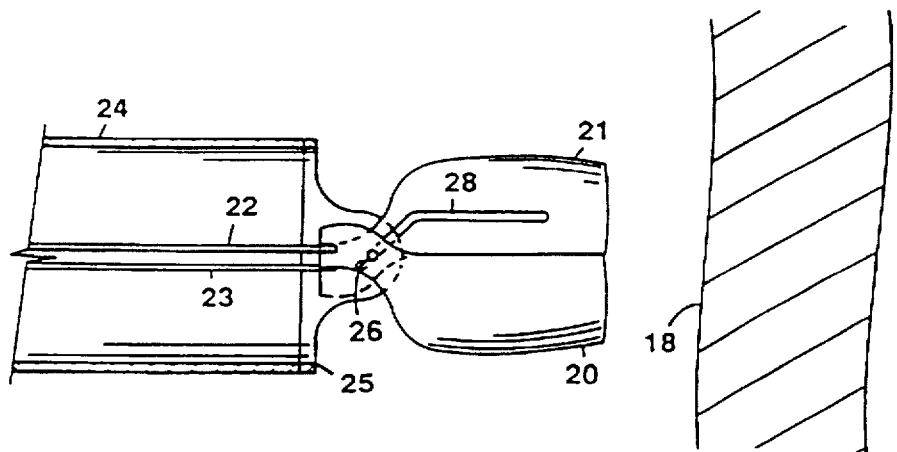
FIGS. 5, 5a–5e illustrate a use of another embodiment.

Referring to FIGS. 5a–5e, particularly FIG. 5, in use, jaws 20, 21 of the device are first brought close to a tissue surface 18 where a sample is to be taken. (In this illustration, the cam slot 28 is positioned near the top of the jaw 21 to maximize the transverse motion).

Figure 5A:
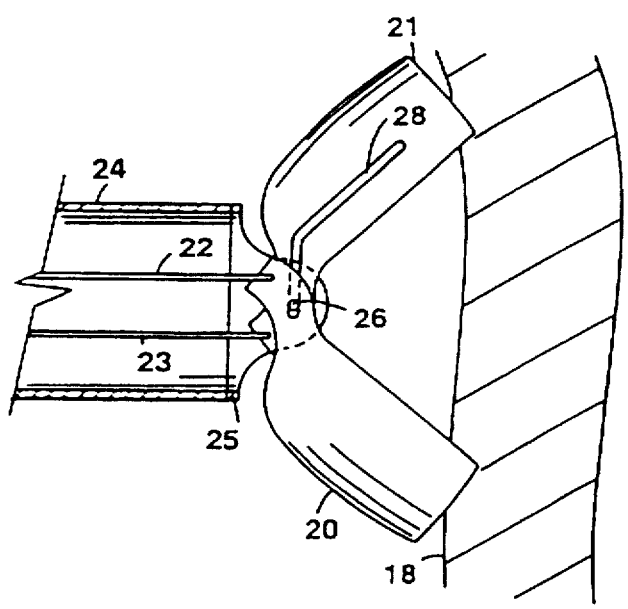

Referring to FIG. 5a, control wires 22, 23 are pushed distally to force open jaw members 20, 21 by acting against the pivot pins 26. With jaws 20, 21 open, the device is advanced so the jaws come in contact with tissue surface 18.

Figure 5B:
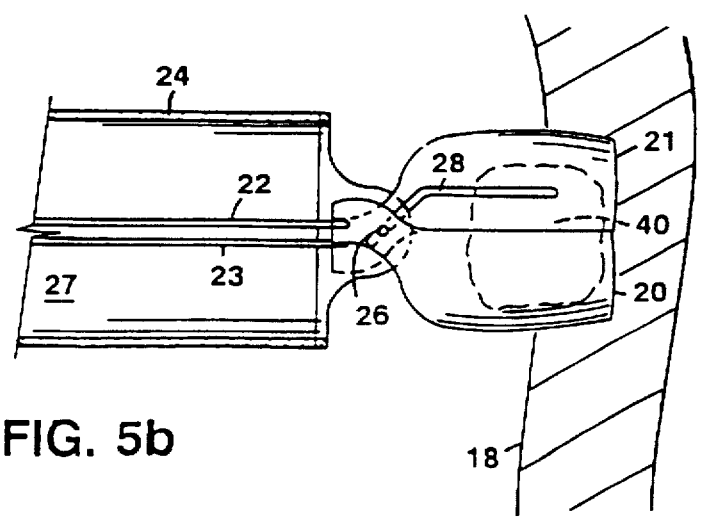

Referring to FIG. 5b, the control wires are pulled proximally to close jaws 20, 21 and to separate a first sample 40 from tissue surface 18.

Figure 5C:
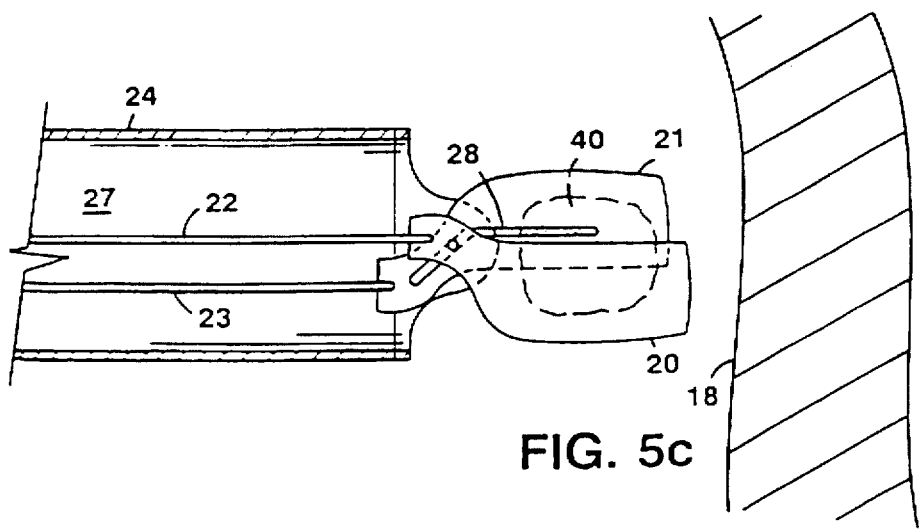
Figure 5D:
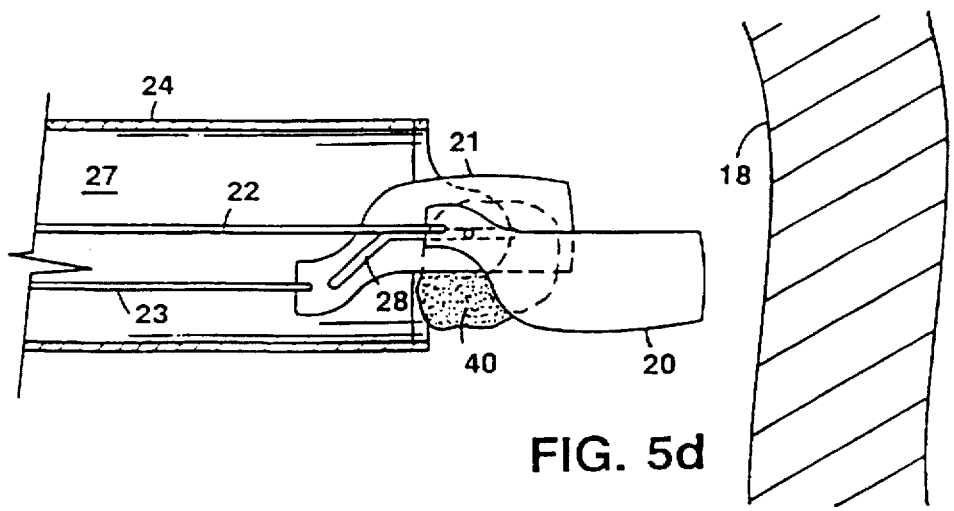

Referring to FIGS. 5c and 5d, the first sample 40 is brought into sample storage space 27 by pulling on control wire 22, moving jaw 21 proximally with respect to jaw 20. Referring particularly to FIG. 5c, cam slot 28 is arranged so that jaw 21 moves transversely into jaw 20 to trap the sample 40. Referring particularly to FIG. 5d, continued proximal movement of control wire 22 moves jaw 21 axially to place the sample 40 in sample storage space 27. Control wire 22 is then pushed distally to return jaw 21 to a position opposing jaw 20.

Figure 5E:
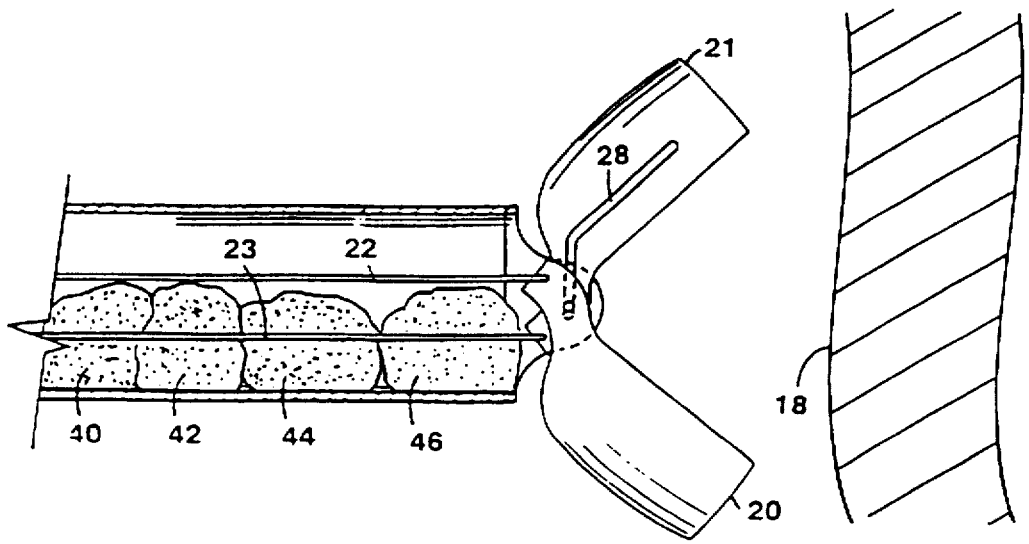

Referring to FIG. 5e, subsequent samples 42–46 can be taken without removing the device from the endoscope by repeating the above sequence. The samples 42–46 are brought into the sample storage space 27 in the order in which they were collected. After sufficient samples have been taken, the device is removed from the endoscope and the samples recovered, e.g. by using a pusher (not shown) inside the sample space 27 to push the samples out through the open jaws.

Figure 6:
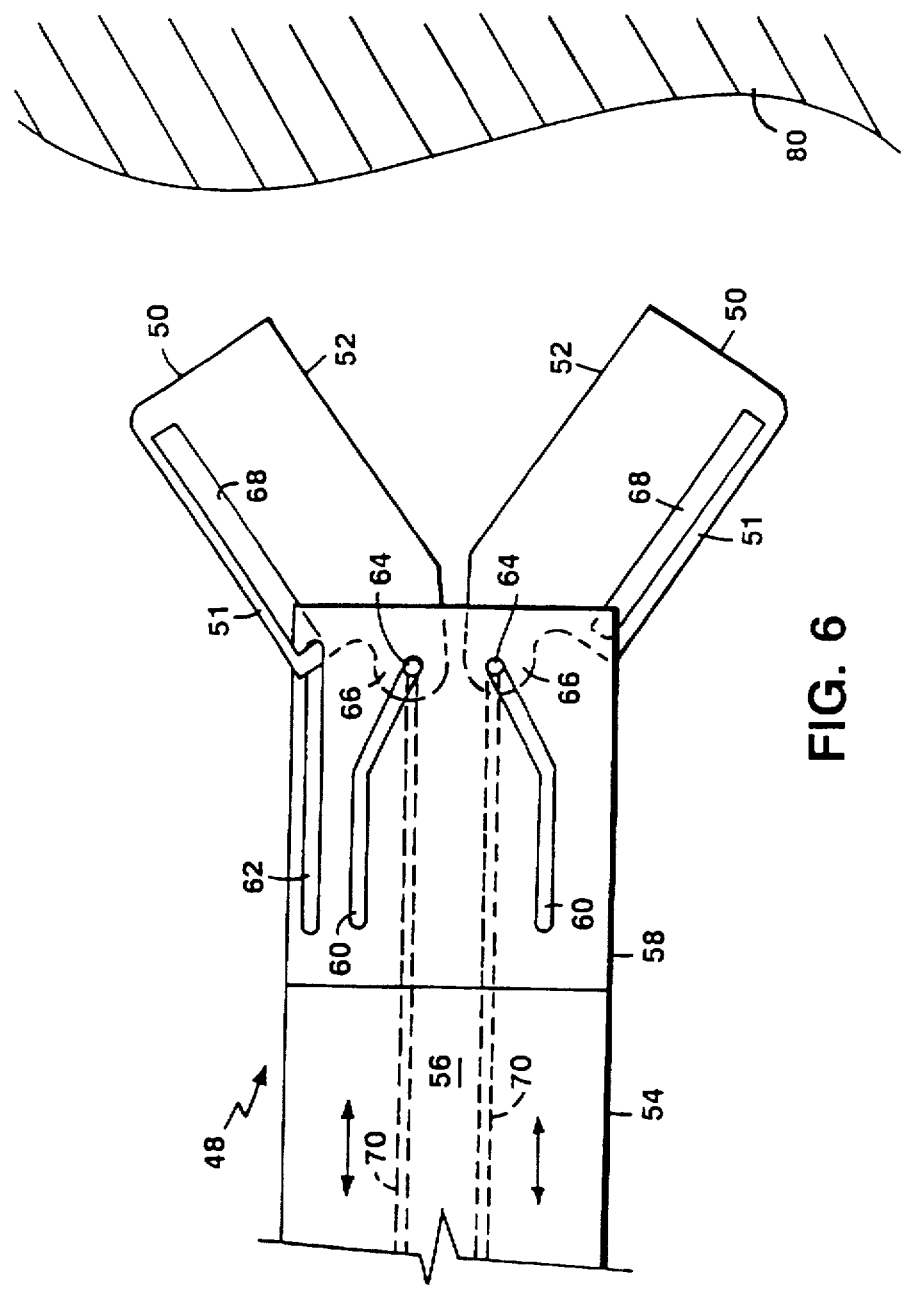
Figure 6A:
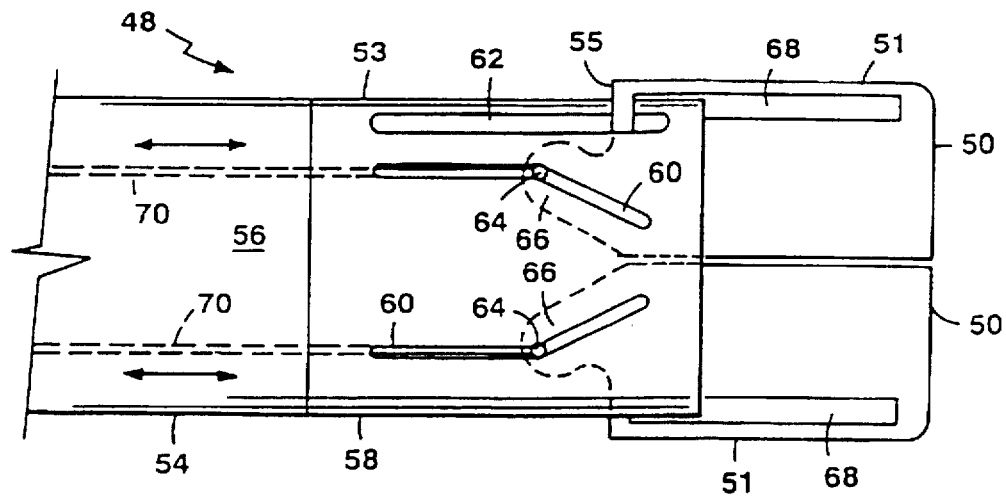
FIG. 6a is a similar view with the jaws closed.
Figure 6B:
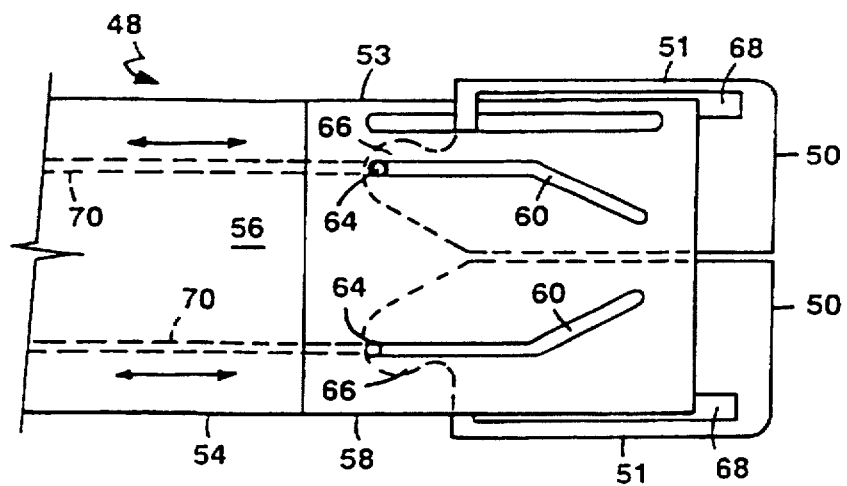
FIG. 6b is a similar view with the jaws retracted.

Referring to FIG. 6–7a in another embodiment the sampling portion 48 includes jaws 50 that can be radially opened (FIG. 6) and closed (FIG. 6a), to take a sample, and then drawn axially proximally, to pull the sample into a storage space 56 (FIG. 6b). (When jaws 50 are in the closed position, surfaces 52 are in contact with one another. The drawings show otherwise for clarity). All or part of surface 52 of jaws 50 may be sharpened or serrated to facilitate cutting. The embodiment includes a relatively flexible proximal sleeve 54 defining most of the storage space 56 and a relatively stiff coupling section 58. The coupling section 58 includes two sets of cam slots for defining the motion of each of the jaws.

Each of the sets includes a cam track 60 on the sides of the coupling section 58 and cam slot 62 that is near the top and bottom of the coupling section 58. The cam track 60 defines a track for pins 64 that are attached to ear-forms 66 extending proximally from the jaws (jaws and ear-forms integrally formed of 0.004 inch stainless steel). The cam slots 62 couple to jaw slots 68 so the top portion 51 of jaws 50 can ride on the outside of the coupling section 58 as the jaws 50 are drawn proximally into the storage space 56. (To assemble the device, the jaw slots 68 are closed (e.g. by welding) at the back portion 55 after the jaws have been aligned and positioned on the device.) The jaws 50 are controlled by control wires 70 (0.004 inch steel cable) that are attached to the interior extensions 72 of the pins 64 (FIG. 7c) and can be extended or withdrawn from outside the body. The coupling section 58 is relatively rigid, e.g. a metal (0.004 inch thick stainless steel), and the sleeve 54 is relatively flexible, e.g. a polymer. The axial length of the coupling section is approximately the same as the jaws 50, e.g. 5–7 mm.

In use, the device is inserted into the body, e.g. through an endoscope, with the jaws retracted into the coupling section 58 (FIG. 6b). The relatively stiff coupling section 58 provides protection for the jaws 50 during delivery into and removal from the body (and thus allows the jaws to be made thinner, cheaper, and more flexible). Moreover, retracting the jaws 50 makes delivery through tortuous passageways easier since the length of the stiff portions of the device is reduced compared to the jaw extended configuration. Once the sampling site is reached, the jaws 50 can be extended out of the coupling section 58 by extending the control wires 70 which causes the pins 64 on the jaw ears-forms 66 to follow the cam track 60 to a point where the track bends (FIG. 6a). At the same time, the top portion 51 of the jaw 50 travels over the top 53 of the coupling section 58 as allowed by the cam slots 62 on the coupling section and jaw slots 68 on the top of the jaws 50. The jaws 50 are opened by continuing to extend the control wires 70, which causes the pins 64 to follow the cam track 60 in a transverse direction. The top of the jaws, having reached the proximal end of jaw slot 68 and the distal end of cam slot 62, pivot about the location where the proximal end of the jaw slot 68 engages the distal end of slot 62 (FIG. 6). The open jaws 50 are pushed forward against the tissue surface 80 where a sample is to be taken (not shown). The jaws 50 are then closed by withdrawing the control wires 70, causing the pins 64 to travel transversely and the jaws 50 to pivot closed about the distal end of the slot 62. With the jaws 50 closed, the sample, now cut and captured between the jaws 50 (not shown), can be pulled proximally by further withdrawing the control wires 70 so the pins 64 follow the axial portion of the cam track 60 and the top portion 51 of the jaws 50 slides over the top portion 53 of the coupling section 58. The sequence above can be repeated to take additional samples without removing the device from the body. Each successive sample is drawn back by the jaws 50, pushing the previous samples proximally into the storage space 56 within sleeve 54. When a sufficient number of samples have been taken, the jaws 50 are retracted into the coupling section 58 to protect them and reduce the axial stiffness, and the device is removed from the body. The samples can be retrieved by opening the jaws and providing gentle suction to draw them from the distal end. Alternatively, a pusher, which can be extended distally from the proximal end of the storage space can be used to push the samples out of the open jaws.

As shown in FIG. 7e, the jaw 50 may be made from flat stock that is stamped, cut out, and then formed into the three dimensional jaw by welding, for example.

In embodiments, optionally, the device can be provided with alternate means to facilitate drawing samples into the storage space, such as an axially moveable barbed spearform that can be extended to pierce the samples and then drawn proximally. A tongue or rake-shaped member can also be provided for this purpose. The jaws can also be moved separately. For example, one jaw can be moved relative to the other jaw to create a shearing action that helps cut tissue from a surface after it has been grasped by the jaws. This reduces the amount of force needed in radial motion to perform the cutting function and thus allows thinner, more flexible jaw construction. Preferably, the jaws are provided with serrated cutting edges when used in this way.

A system for taking multiple biopsy samples is taught in "Instruments for Collecting Multiple Biopsy Specimens", U.S. Ser. No. 062,671, filed May 17, 1993, the entire contents of which is hereby incorporated by reference. Another system is taught in U.S. Ser. No. 08/124,272, filed Sep. 20, 1993, which is also incorporated herein by reference. Another system is taught in U.S. Ser. No. 08/129,653, filed Sep. 30, 1993 which is also incorporated herein by reference. Another system is taught in U.S. Ser. No. 08/146,447, filed Oct. 29, 1993, which is hereby incorporated by reference. Another system is taught in an application entitled "Moveable Sample Tube Multiple Biopsy Sample Device", by Banik et al., filed on the same day as this application, which is hereby incorporated by reference. Another system is taught in an application entitled "Multi-Motion Side-Cutting Multiple Biopsy Sample Device", by Banik and Robinson, filed on the same day as this application, which is also incorporated herein by reference.

Still other embodiments are within the following claims. For example, the radial and axial motion of the jaw could be provided by multiple control wires attached directly to the jaw. One wire could be connected to the distal end of the jaw to control radial motion and another wire connected to the proximal portion of the jaw to control axial motion. The jaw is provided with a straight slot so it can be slid axially into the storage space without transverse motion. These wires may be positioned to extend outside of the tube defining the sample space.

Still further embodiments follow.

What is claimed is:

1. An instrument for obtaining multiple tissue samples from sites within a body while the instrument remains within the body, the instrument comprising:

an elongated flexible portion having a distal end;

a device body defining a storage space proximate the distal end for storing multiple samples; and a distal end sampling assembly having a first cutting member capable of a rotational motion for detaching a tissue sample from the body and of an axial motion for disposing said sample into said storage space.

2. The instrument of claim 1 wherein said first cutting member is a jaw-like member, and said rotational motion causes said jaw-like member to pivot radially outward and inward.

3. The instrument of claim 2 wherein said instrument includes a second jaw-like cutting member capable of rotational motion.

4. The instrument of claim 3 wherein said first jaw-like cutting member moves transversely into a space defined by said second jaw-like member to engage a detached tissue sample.

5. The instrument of claim 1 wherein said device body is a tubular member and said first cutting member is attached to said tubular member via a camming arrangement whereby axial movement of said tubular member relative to said first cutting member generates said rotational and axial motions of said first cutting member.

6. The instrument of claim 5 wherein said cam arrangement includes a slot provided on said cutting member and a pin provided on said tubular member.

7. The instrument of claim 6 wherein said camming arrangement provides opening and closing motions of said first cutting member for detaching a tissue sample, axial motion of said first cutting member for engaging and disposing said sample in said storage space, and axial motion of said first cutting member for returning said first cutting member to a position in preparation for taking another sample.

8. The instrument of claim 2 wherein said device body is a tubular member and said first cutting member is attached to said tubular member via a camming arrangement whereby axial movement of said tubular member relative to said first cutting member generates said rotational and axial motions of said first cutting member.

9. The instrument of claim 8 wherein said cam arrangement includes a slot provided on said cutting member and a pin provided on said tubular member.

10. The instrument of claim 9 wherein said camming arrangement provides opening and closing motions of said first cutting member for detaching a tissue sample, axial motion of said first cutting member for engaging and disposing said sample in said storage space, and axial motion of said first cutting member for returning said first cutting member to a position in preparation for taking another sample.

11. The instrument of claim 3 wherein said device body is a tubular member and said first cutting member is attached to said tubular member via a camming arrangement whereby axial movement of said tubular member relative to said first cutting member generates said rotational and axial motions of said first cutting member.

12. The instrument of claim 11 wherein said cam arrangement includes a slot provided on said cutting member and a pin provided on said tubular member.

13. The instrument of claim 12 wherein said camming arrangement provides opening and closing motions of said first cutting member for detaching a tissue sample, axial motion of said first cutting member for engaging and disposing said sample in said storage space, and axial motion of said first cutting member for returning said first cutting member to a position in preparation for taking another sample.

14. The instrument of claim 3 wherein said second jaw-like member is capable of axial motion.

15. The instrument of claim 14 wherein said first and second jaw-like members are coupled to said elongated flexible portion at a distal end portion that is rigid relative to said flexible portion proximal thereof.

16. The instrument of claim 15 wherein said rigid distal end portion has an axial length that is about equal to or shorter than the axial length of said jaw-like members.

17. The instrument of claim 16 wherein said rigid distal end portion defines a space that has an axial length that is about equal to the axial length of said jaw-like members, and said jaw-like members are moveable proximally within said distal end portion.

18. The instrument of claim 17 wherein said distal end portion has a length of about 5–7 mm.

19. The instrument of claim 4 wherein said device body is a tubular member and said first cutting member is attached to said tubular member via a camming arrangement whereby axial movement of said tubular member relative to said first cutting member generates said rotational, axial and transverse motions of said first cutting member.

20. The instrument of claim 19 wherein said camming arrangement includes a slot provided on said cutting member and a pin provided on said tubular member.

21. The instrument of claim 20 wherein said camming arrangement provides opening and closing motions of said cutting members for detaching said tissue sample, transverse motion of said first cutting member relative to said second cutting member for engaging said sample, axial motion of said first cutting member for disposing said sample in said storage space, and axial motion of said first cutting member for returning said first cutting member to a position in preparation for taking another sample.

22. The instrument of claim 14 wherein said device body is a tubular member and said cutting members are each attached to said tubular member via a camming arrangement whereby axial movement of said tubular member relative to said cutting members generates said rotational and axial motions of said cutting members.

23. The instrument of claim 22 wherein said camming arrangement includes pins provided on said cutting members and slots provided on said tubular member.

24. The instrument of claim 23 wherein said camming arrangement provides opening and closing motions of at least one of said cutting members, axial motions of at least one of said cutting members for engaging and disposing said sample in said storage space, and axial motion of at least one of said cutting members for returning at least one of said cutting members to a position in preparation for taking another sample.

25. The instrument of claim 24 wherein said camming arrangement provides an axial retraction motion for stowing said cutting members within said tubular member.

* * * * *

UNITED STATES PATENT AND TRADEMARK OFFICE
CERTIFICATE OF CORRECTION

PATENT NO. : 5,779,648

DATED : July 14, 1998

INVENTOR(S) : Michael Banik et al.

It is certified that error appears in the above-identified patent and that said Letters Patent is hereby corrected as shown below:

Claim 6, column 7, line 10, "cuffing" should read --cutting--.

Signed and Sealed this

Twenty-seventh Day of October, 1998

Attest:

BRUCE LEHMAN

*Attesting Officer*         *Commissioner of Patents and Trademarks*